United States Patent [19]

Yagi et al.

[11] Patent Number: 5,061,691

[45] Date of Patent: Oct. 29, 1991

[54] ENKEPHALIN ANALOGS

[75] Inventors: Kunio Yagi, Aichi; Yasuyuki Shimohigashi; Hiroaki Kodama, both of Fukuoka; Tomio Ogasawara, Kasugai; Takuya Koshizaka, Kasugai; Masayasu Kurono, Mie, all of Japan

[73] Assignee: Kabushiki Kaisha Vitamin Kenkyuso, Gifu, Japan

[21] Appl. No.: 235,867

[22] Filed: Aug. 23, 1988

[30] Foreign Application Priority Data

Aug. 24, 1987 [JP] Japan .............................. 62-208219
Sep. 24, 1987 [JP] Japan .............................. 62-237278

[51] Int. Cl.$^5$ .................. A61K 37/02; C07K 5/00
[52] U.S. Cl. ...................................... 514/17; 514/18; 530/302; 530/329
[58] Field of Search ............... 530/302, 329, 323; 514/17, 18

[56] References Cited

FOREIGN PATENT DOCUMENTS 0126892 5/1988 Japan .................................. 530/323

OTHER PUBLICATIONS

Gram. "Organic Chemistry" 2nd Ed. McGraw Hill p. 609 (1964).
Hughes et al., "Nature" 258, 577 (1975).
"Protein, Nucleic Acid, Enzyme": 28, 1321 (1983).
Lutz et al., "Eur. J. Pharmacol,", 111, 257 (1985).
Shimohigashi et al., "Peptide Chemistry 1985" p. 51 (1986).

*Primary Examiner*—Jane T. Fan
*Assistant Examiner*—Celia Chang

*Attorney, Agent, or Firm*—Armstrong, Nikaido, Marmelstein, Kubovcik & Murray

[57] ABSTRACT

The invention relates to enkephalin analogs of the formula

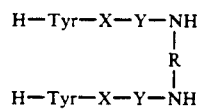

wherein in case of
  X is D-Val, D-Phe, Pro, D-Met, D-Met(O), D-Leu, D-Glu, D-Glu(Obzl), D-Lys, D-Lys(Z), or D-Arg,
  Y is Gly or Phe; and
  R is
   a) a direct bond,
   b) an alkylene group having from 1 to 6 carbon atoms,
   c) o—, m—, or p—phenylene group,
   d) a cycloalkane; or
wherein in case of
  X is D-Ala,
  Y is Phe; and
  R is
   a) a direct bond,
   b) an alkylene group having from 1 to 6 carbon atoms,
   c) o—, m—, or p-phenylene group, or
   d) a cycloalkane,
its salts and hydrates, as well as a therapeutic composition containing at least one of the enkephalin analogs, as an effective component.

11 Claims, No Drawings

ENKEPHALIN ANALOGS

BACKGROUND OF THE INVENTION

1. Field of the Invention

The present invention relates to novel enkephalin analogs, salts and hydrates thereof, as well as a therapeutic composition containing at least one of the enkaphalin analogs.

2. Related Arts

Opiate alkaloids such as morphine induce a strong analgesic effect, but they also cause physical and psychological dependence and addiction as side effects.

Early in 1970, it was confirmed that opiate receptors are localized in mammalian brain; since then, numerous studies have been done to discover endogenous morphine-like substances which can not cause physical and psychological dependence and addiction. Hughes et al. have isolated two pentapeptides as endogenous opioid peptides [Hughes et al., "Nature" 258, 577 (1975)]. Enkephalins produce a weak and short-lived analgesia following intracerebroventricular (i.c.v.) or intravenous (i.v.) administration to mice and rats. $\beta$-Endorphin, which consists of 31 amino acid residues and is a fragment of $\beta$-lipotropin, has marked and long-lived analgesic activity following i.c.v. or i.v. administration. However, it is very difficult to massproduce $\beta$-endorphin, because it is a high molecular weight polypeptide. Therefore, $\beta$-endorphin has not been employed for an analgesic drug.

Shimohigashi et al. have reviewed the studies on synthetic enkephalins [Shimohigashi et al. "Protein, Nucleic acid, Enzyme" 28, 1321 (1983)]. The molecular structure of synthetic enkephalins has been designed to yield enkephalins with the following characteristics: a) lower molecular weight compounds which can be easily prepared, b) higher affinity for the receptors, c) resistance to degradation by enzymes such as aminopeptidase, carboxypeptidase, enkephalinase, and the like, d) easy absorption and diffusion in vivo, e) ability to pass through the blood-brain barrier, f) administration in oral dosage form, g) minimal side effects, and so on. For the chemical modifications in Met- and Leu-enkephalins each amino acid residue in the sequence has been replaced by others or chemically modified, or the enkephalin has been shortened or cyclized; however, no enkephalin analogs have been applied to patients as the analgesic drugs.

In 1980, Rodbard et al. reported symmetrical dimers of enkephalin analogs of the following formula as new synthetic enkephalins (U.S. Pat. No. 4,468,383).

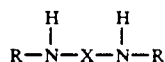

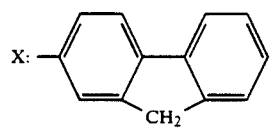

or an alkylene group having from 1 to 22 carbon atoms or a direct bond, and

R: H—Tyr—D—Ala—Gly—Phe—Leu,
H—Tyr—D—Ala—Gly—Phe,
H—Tyr—D—Ala—Gly or
H—Phe—Leu

The compounds in which R is H-Tyr-D-Ala-Gly and X is $C_1$-$C_{22}$-alkylene show more selectivity for $\mu$ than for to $\delta$-receptors, particularly, DTRE$_2$ in which X is $C_2$-alkylene, shows about 400-fold greater selectivity for $\mu$ than for $\delta$ in receptor binding assay [Lutz et al., "Eur. J. Pharmacol." 111, 257 (1985)]. When this compound was assayed using bioassays for opiate activity (GPI and MVD assays), it showed morphine-like activities and greater selectivity for $\mu$ than for $\delta$ [Shimohigashi et al., "Peptide Chemistry 1985" p. 51 (1986)].

SUMMARY OF THE INVENTION

The main object of the invention is to provide novel enkephalin analogs which are easily mass-produced, exhibit opioid activity, and are useful for an analgesic drug.

The concomitant object is to provide novel enkephalin analogs that can exhibit an analgesic effect without influence of dosage form.

According to this invention, the objects can be achieved by providing the enkephalin analogs of the following formula:

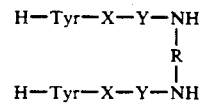

wherein in case of
X is D-Val, D-Phe, Pro, D-Met, D-Met(O), D-Leu, D-Glu, D-Glu(OBzl), D-Lys, D-Lys(Z), or D-Arg,
Y is Gly or Phe; and
R is
a) a direct bond,
b) an alkylene group having from 1 to 6 carbon atoms,
c) o—, m—, or p—phenylene group, or
d) a cycloalkane, or wherein in case of
X is D-Ala,
Y is Phe; and
R is
a) a direct bond,
b) an alkylene group having from 1 to 6 carbon atoms,
c) o—, m—, or p—phenylene group, or
d) a cycloalkane,
its salts and hydrates.

The compound of this invention can be prepared by the method described in EXAMPLES (Examples 1 to 12) given later or by the general method as described by Izumiya et al. [ translated as "Basis and experiments for peptide synthesis" Maruzen Co., Ltd. Japan (1985)]. The compound of this invention can be administered as pharmaceutically acceptable salts such as the hydrochloride, sulfate, sulfonate, phosphate, citrate, benzoate, acetate, propionate, lactate, maleate, malate, succinate, or tartrate.

All of the pharmaceutically acceptable dosage forms may be suitable to prepare a drug containing the compound of this invention, its salt, or hydrate as an active ingredient. The compound can be administered in such oral dosage forms as tablets, capsules, powders, granules, suspensions, or solutions. They can be administered in such non oral dosage forms as sterilized solutions or suspensions. To the compound may be added pharmaceutically acceptable bulking agents, smoothing agents, antiseptics, stabilizers or other additives for dosage forms.

The dosage regimen of the compound according to the invention is selected by taking various factors including the type and severity of symptoms, age, weight, and other conditions of patients, into consideration.

PREFERRED EMBODIMENTS OF THE INVENTION

The following abbreviations are used: Tyr, tyrosine; Ala, alanine; Gly, glycine; Met, methionine; Ser, serine; Thr, threonine; Phe, phenylalanine; Pro, proline; Leu, leucine; NMePhe, N-methylphenylalanine; Gly-ol, glycinol; Boc, tert-butoxycarbonyl; Bzl, benzyl; EDC.HCl, 1-ethyl-3-(3-dimethylaminopropyl) carbodiimide hydrochloride; HOBt, 1-hydroxybenzotriazole; DMF, N,N-dimethylformamide; Z, carbobenzoxy; TFA, trifluoroacetic acid; EtOAc, ethyl acetate; Et$_3$N, triethylamine; HF, hydrogen fluoride.

EXAMPLE 1

Synthesis of Boc-DTRE-φ (o—, m—, or p—)

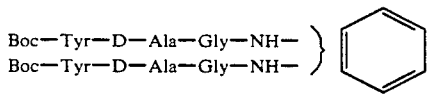

To a solution of Boc-Tyr-D-Ala-Gly-OH (1.1 mmol) and o—, m—, or p—phenylenediamine (0.5 mmol) in DMF were added HOBt (1.3 mmol) and EDC.HCl (1.2 mmol) at −10° C., followed by reaction at room temperature for 2 days. The solvent was evaporated in vacuo. The residual oil was solidified by adding cold water, washed with 4% NaHCO$_3$, 5% KHSO$_4$, and water, and dried over P$_2$O$_5$ in a desiccator. The dried powder was dissolved in DMF (1 ml) and subjected to gel filtration on a column (1.8×100 cm) of Sephadex LH-20 in DMF. The fractions containing the desired compound were pooled and the solvent was evaporated in vacuo. The residue was dissolved in 1 ml of CHCl$_3$-MeOH (9:1, v/v) and subjected to a silica gel column (2.2×65 cm), followed by elution with the same solvent. The fractions containing the desired compound were pooled and the solvent was evaporated in vacuo. The desired compound was crystallized from DMF-EtOAc-diethyl ether and recrystallized from the same solvent.

EXAMPLE 2

Synthesis of DTRE-φ (o—, m—, or p—)

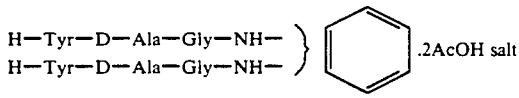

Boc-DTRE-φ (o—, m—, or p—)(0.2 mmol) was dissolved in TFA at 0° C. After 30 min, the solvent was evaporated in vacuo. The residue was dissolved in 30% AcOH, and subjected to gel filtration on a Sephadex G-15 column (2.0×140 cm) in the same solvent. The fractions containing the desired compound were pooled and the solvent was evaporated in vacuo. The residue was dissolved in distilled water and the solvent was evaporated in vacuo. This procedure was repeated to remove AcOH from the solution. The residue was dissolved in distilled water. The desired compound was obtained by lyophilization.

EXAMPLE 3

Synthesis of Boc-DTRE-CH

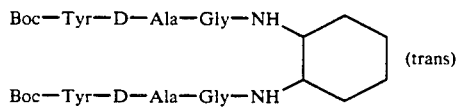

To a solution of Boc-Tyr-D-Ala-Gly-OH (1.1 mmol) and trans-1,2-diaminocyclohexane (0.5 mmol) in DMF were added HOBt (1.3 mmol) and EDC.HCl (1.2 mmol) at −10° C., followed by stirring at room temperature for 2 days. The solvent was evaporated in vacuo. The residual oil was dissolved in 30 ml of EtOAc and washed with 5% KHSO$_4$, 4% NaHCO$_3$, and a saturated NaCl solution. The residue was dried over Na$_2$SO$_4$. Na$_2$SO$_4$ was removed by filtration and the filtrate was evaporated to dryness in vacuo. The residue was dissolved in 1 ml of CHCl$_3$-MeOH (9:1, v/v), subjected to a silica gel column (0.9×40 cm), and aluted with the same solvent. The fractions containing the desired compound were pooled and the solvent was evaporated in vacuo to dryness. The desired compound was crystallized from EtOAc-diethyl etherpetroleum ether.

EXAMPLE 4

Synthesis of DTRE-CH

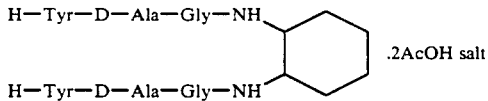

Boc-DTRE-CH (50 μmol) was dissolved in TFA at 0° C. After 30 min, the solvent was evaporated in vacuo. The residue was dissolved in 1 ml of 30% AcOH, subjected to gel filtration on a Sephadex G-15 column (2.0×100 cm) in the same solvent. The fractions containing the desired compound were pooled and the solvent was evaporated in vacuo. The residue was dissolved in distilled water and the solvent was evaporated in vacuo. This procedure was repeated to remove AcOH from the solution. The residue was dissolved in distilled water. The desired compound was obtained by lyophilization.

Physical properties of the substance obtained Examples 1 to 4 by each were given in following Table 1 and 2.

TABLE 1

| Peptides | Yield (%) | Melting point (°C.) | Specific rotation $[\alpha]_D^{20}$ | $Rf^1$ | $Rf^2$ | Elemental analysis observed | | | Elemental analysis calculated | | |
|---|---|---|---|---|---|---|---|---|---|---|---|
| | | | | | | C | H | N | C | H | N |
| Boc—DTRE-φ-(o) | 53 | 156–158 | −3.4[a] | 0.62 | 0.74 | 58.70 | 6.86 | 12.35 | 58.72 | 6.61 | 12.45 (0.5 H$_2$O) |
| Boc—DTRE-φ-(m) | 58 | 157–159 | −18.1[a] | 0.56 | 0.63 | 58.12 | 6.72 | 12.15 | 58.13 | 6.65 | 12.33 (H$_2$O) |
| Boc—DTRE-φ-(p) | 43 | 158–159 | −27.1[a] | 0.54 | 0.59 | 58.36 | 6.63 | 12.26 | 58.13 | 6.65 | 12.33 (H$_2$O) |
| Boc—DTRE—CH | 17 | 146–148 | −17.9[b] | 0.63 | 0.73 | 57.69 | 7.28 | 12.20 | 57.75 | 7.27 | 12.25 (H$_2$O) |

[a] c 1.0, DMF;
[b] c 1.0, MeOH
$Rf^1$: CHCl$_3$—MeOH (5:1, v/v)
$Rf^2$: CHCl$_3$—MeOH—AcOH (50:10:2, v/v)

TABLE 2

| Peptides | Yield (%) | Melting point (°C.) | Specific[a] rotation $[\alpha]_D^{20}$ | $Rf^3$ | $Rf^4$ | Amino acid composition | | |
|---|---|---|---|---|---|---|---|---|
| | | | | | | Tyr | Ala | Gly |
| DTRE-φ (o) | 78 | 128–129 | +47.2 | 0.54 | 0.56 | 1.96 | 2.00 | 2.02 |
| DTRE-φ (m) | 57 | 143–145 | +24.2 | 0.52 | 0.55 | 1.98 | 2.00 | 2.00 |
| DTRE-φ (p) | 83 | 160–161 | +35.8 | 0.48 | 0.54 | 1.96 | 2.00 | 2.06 |
| DTRE—CH | 98 | 131–133 | +42.3 | 0.55 | 0.58 | 2.00 | 2.00 | 2.08 |

[a] c 0.5, 95% AcOH
$Rf^3$: n-BuOH—AcOH—pyridine—H$_2$O (4:1:1:2, v/v)
$Rf^4$: 0.1% AcOH-n-BuOH—pyridine (11:5:3, v/v, upper layer)

EXAMPLE 5

Synthesis of (Boc-Phe-NH-CH$_2$-)$_2$

To a solution of Boc-Phe-OH (11 mmol) and ethylene diamine (NH$_2$-CH$_2$-CH$_2$-NH$_2$) (5 mmol) in DMF were added HOBt (13 mmol) and EDC.HCl (12 mmol), followed by stirring at room temperature for 2 days. The solvent was evaporated in vacuo. The residual oil was solidified by adding cold water, washed with 4% NaHCO$_3$, 5% KHSO$_4$, and water on a glass filter and dried over P$_2$O$_5$ in a desiccator. The dried powder was dissolved in 5 ml of DMF and subjected to gel filtration on a Sephadex LH-20 column (5×110 cm) in DMF. The fractions containing the desired compound were pooled and the solvent was evaporated in vacuo to dryness. The desired compound was crystallized from DMF-MeOH-diethyl ether and recrystallized from the same solvent.

Yield: 89%
Melting point: 197°–198° C.,
Specific rotation: $[\alpha]_D$ = −2.67° (c 0.53, DMF),
HPTLC: $Rf^1$ value; 0.91 (CHCl$_3$-MeOH=9:1, v/v), $Rf^2$ value; 0.72 (CHCl$_3$-MeOH-AcOH=95:5:1, v/v),
Elemental analysis: calculated; C, 64.96; H, 7.63; N, 10.10, observed; C, 64.98; H, 7.62; N, 10.03.

EXAMPLE 6

Synthesis of (H-Phe-NH-CH$_2$-)$_2$.2TFA salt (Boc-Phe-NH-CH$_2$-)$_2$ (3 mmol) was dissolved in TFA at 0° C. After 30 min, the solvent was evaporated in vacuo. The residue was solidified by adding diethyl ether and dried over KOH in a desiccator.

Yield: 99%,
Melting point: 213°–217° C. (decomposition)
Specific rotation: $[\alpha]_D$ = +63.8° (c 0.16, 95% AcOH),
HPTLC: $Rf^3$ value; 0.05 (n-BuOH-AcOH-H$_2$O=4:1:5, v/v, upper layer), $Rf^4$ value; 0.56 (n-BuOH-AcOH-pyridine-H$_2$O=4:1:1:2, v/v), $Rf^5$ value; 0.60 (0.1% AcOH-n-BuOH-pyridine=11:5:3, v/v, upper layer),
Elemental analysis: calculated; C, 49.49; H, 4.85; N, 9.62, observed; C, 49.60; H, 4.91; N, 9.56.

EXAMPLE 7

Synthesis of (Boc-Tyr-D-Ala-Phe-NH-CH$_2$-)$_2$

To a solution of Boc-Tyr-D-Ala-OH (1.1 mmol), (H-Phe-NH-CH$_2$-)$_2$.2TFA(0.5 mmol), and Et$_3$N (1.0 mmol) in DMF were added HOBt (1.3 mmol) and EDC.HCl (1.2 mmol) at −10° C., followed by stirring at room temperature for 2 days. The solvent was evaporated in vacuo. The residual oil was solidified by adding cold water, washed with 4% NaHCO$_3$, 5% KHSO$_4$, and water on a glass filter and dried over P$_2$O$_5$ in a desiccator. The dried powder was dissolved in 1 ml of DMF and subjected to gel filtration on a Sephadex LH-20 column (2×140 cm) in DMF. The fractions containing the desired compound were pooled and the solvent was evaporated in vacuo to dryness. The desired compound was crystallized from DMF-EtOAc-diethyl ether and recrystallized from the same solvent.

EXAMPLE 8

Synthesis of (Boc-Xxx-Phe-NH-CH$_2$-)$_2$ (Xxx=Pro, D-Val, D-Leu, D-Met(O), or D-Glu(OBzl))

To a solution of Boc-Xxx—OH (1.1 mmol), (H-Phe-NH-CH$_2$-2.2TFA (0.5 mmol) and Et$_3$N (1.0 mmol) in DMF were added HOBt (1.3 mmol) and EDC.HCl (1.2 mmol) at −10° C., followed by stirring at room temperature for 2 days. The solvent was evaporated in vacuo. The residual oil was solidified by adding cold water, washed with 4% NaHCO$_3$, 5% KHSO$_4$, and water on a glass filter and dried over P$_2$O$_5$ in a desiccator. The dried powder was dissolved in 1 ml of DMF and subjected to gel filtration on a Sephadex LH-20 column (2×140 cm) in DMF. The fractions containing the desired compound were pooled and the solvent was evaporated in vacuo to dryness. The desired compound was crystallized from DMF-EtOAc-diethyl ether and recrystallized from the same solvent.

EXAMPLE 9

Synthesis of (H-Xxx-Phe-NH-CH$_2$-)$_2$.2TFA
salt(Xxx=Pro, D-Val, D-Leu, D-Met(O), or
D-Glu(OBzl))

(Boc-Xxx-Phe-NH-CH$_2$-)$_2$ (2 mmol) was dissolved in TFA at 0° C. After 30 min, the solvent was evaporated in vacuo. The residue was solidified by adding diethyl ether and dried over KOH in a desiccator.

EXAMPLE 10

Synthesis of (Boc-Tyr-Xxx-Phe-NH-CH$_2$-)$_2$.2TFA salt
(Xxx=Pro, D-Val, D-Leu, D-Met(O), or
D-Glu(OBzl))

To a solution of Boc-Tyr-OH (1.1 mmol), (H-Xxx-Phe-NH-CH$_2$-)$_2$.2TFA(0.5 mmol) and Et$_3$N (1.0 mmol) in DMF were added HOBt (1.3 mmol) and EDC.HCl (1.2 mmol) at −10° C., followed by stirring at room temperature for 2 days. The solvent was evaporated in vacuo. The residual oil was solidified by adding cold water, washed with 4% NaHCO$_3$, 5% KHSO$_4$, and water on a glass filter and dried over P$_2$O$_5$ in a desiccator. The dried powder was dissolved in 1 ml of DMF and subjected to gel filtration on a Sephadex LH-20 column (2×140 cm) in DMF. The fractions containing the desired compound were pooled and the solvent was evaporated in vacuo to dryness. The desired compound was crystallized from DMF-EtOAc-diethyl ether and recrystallized from the same solvent.

EXAMPLE 11 evaporated in vacuo. The residue was dissolved in 1 ml of 30% AcOH, subjected to a Sephadex G-15 column (2.0×100 cm), and eluted with the same solvent. The fractions containing the desired compound were pooled and the solvent was evaporated in vacuo. The residue was dissolved in distilled water and the solvent was evaporated. This procedure was repeated to remove AcOH. The residue was dissolved in distilled water. The desired compound was obtained by lyophilization.

EXAMPLE 12

Synthesis of (H-Tyr-D-Glu-Phe-NH-CH$_2$)$_2$.2TFA salt (Boc-Tyr-D-Glu(OBzl)-Phe-NH-CH$_2$-)$_2$ (0.4 mmol) was dissolved in TFA at 0° C. After 30 min, the solvent was evaporated in vacuo. The residue was solidified by adding diethyl ether. The powder was dried over KOH in a desiccator. The powder was treated with HF in the presence of 10% anisol at 0° C. for 1 hr. The solvent was evaporated in vacuo. The residue was dried over KOH in a desiccator. The residual oil was dissolved in 10% AcOH, washed with diethyl ether, subjected to a Sephadex G-15 column (2.0×100 cm), and eluted with 30% AcOH. The fractions containing the desired compound were pooled and the solvent was evaporated in vacuo. The residue was dissolved in distilled water and the solvent was evaporated. This procedure was repeated to remove AcOH. The residue was dissolved in distilled water. The desired compound was obtained by lyophilization.

The physical properties of the substances obtained by Examples 7-12 are shown in following Tables 3-6.

TABLE 3

| Xxx | Yield (%) | Melting point (°C.) | Specific rotation $[\alpha]_D^{20}$ (c 0.49–0.59, DMF) | Rf$^1$ | Rf$^2$ | Elemental analysis observed C | H | N | calculated C | H | N |
|---|---|---|---|---|---|---|---|---|---|---|---|
| Pro | 96 | 139–140 | −55.9 | 0.48 | 0.24 | 63.52 | 7.46 | 11.15 | 63.39 | 7.58 | 11.09 (0.5 H$_2$O) |
| D—Val | 98 | 236–237 (dec.) | −14.4 | 0.90 | 0.46 | 62.45 | 7.88 | 10.96 | 62.32 | 8.11 | 10.90 (H$_2$O) |
| D—Leu | 96 | 215–216 | −8.1 | 0.91 | 0.48 | 64.50 | 8.25 | 10.71 | 64.59 | 8.26 | 10.76 |
| D—Met(O) | 80 | 188–190 | −16.7 | 0.33 | 0.09 | 55.86 | 7.15 | 9.87 | 55.99 | 7.17 | 9.79 (0.5 H$_2$O) |
| D—Glu(OBzl) | 97 | 200–202 | −12.9 | 0.93 | 0.48 | 65.13 | 6.89 | 8.36 | 65.30 | 6.90 | 8.46 |

Rf$^1$: CHCl$_3$—MeOH (9:1, v/v)
Rf$^2$: CHCl$_3$—MeOH—AcOH (95:5:1, v/v)

Synthesis of (H-Tyr-Xxx-Phe-NH-CH$_2$-)$_2$.2TFA salt
(Xxx=Pro, D-Val, D-Leu, D-Met(O), or D-glu(OBzl))

(Boc-Tyr-Xxx-Phe-NH-CH$_2$-)$_2$(0.4 mmol) was dissolved in TFA at 0° C. After 30 min, the solvent was

TABLE 4

| Xxx | Yield (%) | Melting point (°C.) | Specific rotation $[\alpha]_D^{20}$ (c 0.46–0.63, 95% AcOH) | Rf$^3$ | Rf$^4$ | Rf$^5$ | Elemental analysis observed C | H | N | calculated C | H | N |
|---|---|---|---|---|---|---|---|---|---|---|---|---|
| Pro | 100 | 175–177 | −8.6 | 0.29 | 0.78 | 0.80 | 49.30 | 5.21 | 9.88 | 49.16 | 5.82 | 10.12 (3 H$_2$O) |
| D—Val | 100 | 110–111 | −18.9 | 0.28 | 0.79 | 0.81 | 49.33 | 5.89 | 10.06 | 49.45 | 6.23 | 10.18 (2.5 H$_2$O) |
| D—Leu | 91 | 147–148 | −18.0 | 0.05 | 0.56 | 0.63 | 52.43 | 6.40 | 10.23 | 52.29 | 6.34 | 10.16 (H$_2$O) |
| D—Met(O) | 100 | 212–213 | −9.6 | 0.29 | 0.80 | 0.81 | 45.86 | 5.30 | 9.35 | 45.63 | 5.41 | 9.39 (H$_2$O) |
| D—Glu(OBzl) | 100 | 197–198 | −15.0 | 0.16 | 0.61 | 0.62 | 55.78 | 5.36 | 8.09 | 55.97 | 5.38 | 8.16 (0.5 H$_2$O) |

Rf$^3$: n-BuOH—AcOH—H$_2$O (4:1:5, v/v, upper layer)
Rf$^4$: n-BuOH—AcOH—pyridine—H$_2$O (4:1:1:2, v/v)
Rf$^5$: 0.1% AcOH-n-BuOH—pyridine (11:5:3, v/v, upper layer)

TABLE 5

| Xxx | Yield (%) | Melting point (°C.) | Specific rotation $[\alpha]_D^{20}$ (c 0.51–0.63, DMF) | Rf[6] | Rf[7] | Elemental analysis observed C | H | N | calculated C | H | N |
|---|---|---|---|---|---|---|---|---|---|---|---|
| Pro | 44 | 129–132 | −42.8 | 0.63 | 0.68 | 63.05 | 7.00 | 10.46 | 63.20 | 7.04 | 10.17 (1.5 $H_2O$) |
| D—Val | 70 | 238–241 | −28.8 | 0.62 | 0.68 | 63.63 | 7.48 | 10.31 | 63.48 | 7.35 | 10.21 ($H_2O$) |
| D—Leu | 82 | 151–153 | −10.9 | 0.64 | 0.69 | 63.66 | 7.39 | 10.04 | 63.53 | 7.55 | 9.88 (1.5 $H_2O$) |
| D—Met(O) | 88 | 221–222 | −11.0 | 0.50 | 0.50 | 58.33 | 6.77 | 9.41 | 58.37 | 6.76 | 9.39 ($H_2O$) |
| D—Glu(OBzl) | 94 | 189–190 | −16.2 | 0.70 | 0.76 | 64.64 | 6.61 | 8.49 | 64.65 | 6.63 | 8.38 ($H_2O$) |
| D—Ala | 86 | 160–161 | −13.2 | 0.59 | 0.78 | 62.52 | 6.89 | 10.75 | 62.29 | 6.97 | 10.76 ($H_2O$) |

Rf[6]: $CHCl_3$—MeOH (5:1, v/v)
Rf[7]: $CHCl_3$—MeOH—AcOH (50:10:2, v/v)

TABLE 6

| Xxx | Yield (%) | Melting point (°C.) | Specific rotation $[\alpha]_D^{20}$ (c 0.49–0.58, 95% AcOH) | Rf[3] | Rf[4] | Rf[5] | Amino acid composition Tyr | Xxx | Phe |
|---|---|---|---|---|---|---|---|---|---|
| Pro | 76 | 116–119 | −22.7 | 0.03 | 0.42 | 0.42 | 1.96 | 2.02 | 2.00 |
| D—Val | 91 | 206–207 | +40.4 | 0.16 | 0.70 | 0.66 | 1.98 | 2.04 | 2.00 |
| D—Leu | 100 | 162–165 | +43.8 | 0.21 | 0.76 | 0.70 | 2.00 | 2.04 | 2.00 |
| D—Met(O) | 100 | 107–108 | +32.9 | 0.04 | 0.37 | 0.33 | 1.94 | 2.00 | 2.00 |
| D—Glu(OBzl) | 100 | 114–115 | +54.9 | 0.21 | 0.76 | 0.71 | 1.96 | 2.02[a] | 2.00 |
| D—Glu | 95 | 189–190 | +46.2 | 0.21 | 0.74 | 0.74 | 1.98 | 2.06 | 2.00 |
| D—Ala | 89 | 128–131 | +52.0 | 0.04 | 0.57 | 0.62 | 2.00 | 2.02 | 2.00 |

[a]Glu(OBzl): Glu was detected by hydrolysis.
Rf[3], Rf[4], Rf[5]: The composition of each solvent system was described in Table 4.

TEST EXAMPLE

Biological activities in two isolated smooth muscle preparations: the guinea pig ileum (GPI) and the mouse vas deferens (MVD)

The GPI assay was carried out according to the method reported by Kosterlitz et al. ["Br. J. Pharmacol." 39, 398 (1970)]. A male Hartley guinea pig was sacrificed by cutting its jugular vein and subjected to an abdominal operation to remove its ileum as a piece of about 40 cm in length from a region 10 cm apart from ileocecal region. Then it was immediately immersed in low $Mg^{2+}$ modified Krebs-bicarbonate solution (118 mM NaCl, 4.75 mM KCl, 2.54 mM $CaCl_2$, 1.19 mM $KH_2PO_4$, 0.12 mM $MgSO_4$, 25 mM $NaHCO_3$, 11 mM glucose). The myenteric plexus-longitudinal muscle strips were prepared according to the method reported by Paton et al., ["J. Physiol." (London) 194, 13, (1968)]. The strip was mounted in a 7 ml bath in the above-mentioned solution gassed with 95% $O_2$–5% $CO_2$ at 35° C. and stimulated coaxially with rectangular pulses of 1-msec duration at a frequency of 0.1 Hz at supramaximal voltage (70 Volts) to record the resulting contraction through a trasducer. The concentration required to produce a half-maximal effect ($IC_{50}$) was calculated for the morphine-like activity of the sample.

The MVD assay was carried out according to the method reported by Hughes et al. ["Br. J. Pharmacol." 53, 371 (1975)]. An albino ddY mouse was decapitated and phlebotomized. Then it was immediately subjected to an abdominal operation to remove its vas deferens. The latter was immersed in modified Krebsbicarbonate solution (118 mM NaCl, 4.75 mM KCl, 2.54 mM $CaCl_2$, 1.19 mM $KH_2PO_4$, 25 mM $NaHCO_3$, 11 mM glucose), and adhering fat and blood vessels were removed. After being washed with the above-mentioned solution, the tissue was mounted in a 7 ml bath in the same solution gassed with 95% $O_2$–5% $CO_2$ at 35° C. and stimulated electrically (70 V, 0.1 Hz, 1 msec) by passage of current between an intramural platinum wire and a ring (10 mm wide) of platinum foil fixed to the top of the organ bath to record the resulting contraction through a transducer.

The concentration required to produce a half-maximal effect ($IC_{50}$) was calculated for the morphine-like activity of the sample.

Following Table 7 shows the biological activities of the compound of the present invention by the GPI and MVD assays. Table 7 suggests that the compound of the present invention can inhibit the contraction of GPI and MVD caused by an electric stimulation. The ratio of $IC_{50}$ in MVD assay to that in GPI assay suggests that the compound of the present invention would have a higher affinity for the receptor which is bound preferentially by morphine.

TABLE 7

| Materials | $IC_{50}$ (μM) GPI | MVD | Activity ratio MVD/GPI |
|---|---|---|---|
| The compound of this invention | | | |
| DTRE-φ (o) | 0.20 | 0.95 | 4.8 |
| DTRE-φ (m) | 51 | 265 | 5.2 |
| DTRE-φ (p) | 640 | 600 | 0.94 |
| DTRE—CH (trans) | 0.46 | 4.2 | 9.1 |
| (H—Tyr—Xxx—Phe—NH—$CH_2$—)$_2$ | | | |
| Xxx = D—Ala | 0.042 | 0.079 | 1.9 |
| D—Val | 0.24 | 0.13 | 0.54 |
| D—Leu | 1.7 | 0.25 | 0.15 |

TABLE 7-continued

| Materials | IC$_{50}$ (μM) GPI | MVD | Activity ratio MVD/GPI |
|---|---|---|---|
| Pro | 0.11 | 1.2 | 11 |
| D—Met (O) | 0.051 | 0.21 | 4.1 |
| D—Glu | 0.49 | 2.4 | 4.9 |
| Controls | | | |
| Morphiceptin | 0.21 | 1.2 | 5.7 |
| H—Tyr—Pro—Phe—Pro—NH$_2$ | | | |
| DAGO | 0.0064 | 0.078 | 12 |
| H—Tyr—D—Ala—Gly—NMePhe—Gly—ol | | | |
| Leu—enkephalin | 0.13 | 0.006 | 0.046 |
| H—Tyr—Gly—Gly—Phe—Leu—OH | | | |
| DADLE | 0.019 | 0.00036 | 0.019 |
| H—Tyr—D—Ala—Gly—Phe—D—Leu—OH | | | |
| DTRE$_2$* | 0.44 | 2.7 | 6.1 |
| (H—Tyr—D—Ala—Gly—NH—CH$_2$—)$_2$ | | | |

*Shimohigashi et al., "Peptide Chemistry 1985" p. 51 (1986).

DRUG PREPARATION EXAMPLE 1

Capsules

The compound acording to the invention (Example 1, R=o-phenylene) (50 mg) was added to wheat starch (150 mg) to prepare granules in a conventional manner. The granules (200 mg) were filled in capsules (No. 2) made from gelation (1.0 kg), distilled water (1.5 kg), syrup (0.15 kg) and gum arabic (0.20 kg) to obtain capsuled drug.

DRUG PREPARATION EXAMPLE 2

Dry powder for injection

Prescription:

| The compound (Example 1, R = o-phenylene) | 10 (mg) |
|---|---|
| D-Mannitol | 40 |
| NaCl | 4 |

The components were dissolved in a small amount of distilled water. The solution was aseptically charged in a vail, freeze dried to prepare dry powder sealed in the vail.

The dry powder shall be dissolved in distilled water (2 ml) and then injected to a patient. The solution for injection has an osmotic pressure substantially same with that of the physiological saline solution.

DRUG PREPARATION EXAMPLE 3

Dry powder for injection

Prescription:

| The compound (Example 11) | 10 (mg) |
|---|---|
| D-Mannitol | 40 |
| NaCl | 4 |

The components were dissolved in a small amount of distilled water. The solution was aseptically charged in a vial, freeze-dried to prepare dry powder sealed in the vial.

The dry powder shall be dissolved in distilled water (2 ml) and then injected to a patient. The solution for injection has an osmotic pressure substantially same with that of the physiological saline solution.

What is claimed is:

1. An enkephalin analog of the formula

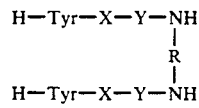

wherein X is D-Ala,D-Val,D-Phe, Pro,D-Met,D-met(O), D-Leu, D-Glu, D-Glu(OBzl), D-Lys, D-Lys(Z) or D-Arg; and Y is Phe; Phe; and R is
 a) a direct bond,
 b) an alkylene group having from 1 to 6 carbon atoms,
 c) an o—, m—, or p—phenylene group, or
 d) a cycloalkane;
or a salt or hydrate thereof.

2. An enkephalin analog according to claim 1, wherein R is a direct bond.

3. An enkephalin analog according to claim 1, wherein R is ethylene.

4. An enkephalin analog according to claim 1, wherein R is o-phenylene.

5. An enkephalin analog according to claim 1, wherein R is m-phenylene.

6. An enkephalin analog according to claim 1, wherein R is p-phenylene.

7. An enkephalin analog according to claim 1, wherein R is cis-cyclopropane or trans-cyclopropane.

8. An enkephalin analog according to claim 1, wherein R is cis-1,2-cyclobutane, trans-1,2-cyclobutane, cis-1,3-cyclobutane or trans 1,3-cylobutane.

9. An enkephalin analog according to claim 1, wherein R is cis-1,2-cyclopentane, trans-1,2-cyclopentane, cis-1,3-cyclopentane or trans-1,3-cyclopentane.

10. An enkephalin analog according to claim 1, wherein R is cis-1,2-cyclohexane, trans-1,2-cyclohexane, cis-1,3-cyclohexane, trans-1,3-cyclohexane, cis-1,4-cyclohexane or trans-1,4-cyclohexane.

11. An pharmaceutical composition comprising an analgesic effective amount of an enkephalin analog of the formula

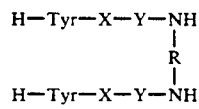

wherein X is D-Ala D-Val,D-Phe, Pro,D-Met,D-met(O), D-Leu, D-Glu, D-Glu(OBzl), D-Lys, D-Lys(Z) or D-Arg; and Y is Phe; Phe; and R is
 a) a direct bond,
 b) an alkylene group having from 1 to 6 carbon atoms,
 c) an o—, m—, or p—phenylene group, or
 d) a cycloalkane; or a salt or hydrate thereof.

* * * * *

UNITED STATES PATENT AND TRADEMARK OFFICE
CERTIFICATE OF CORRECTION

PATENT NO. : 5,061,691
DATED : October 29, 1991
INVENTOR(S) : Kunio YAGI et al

It is certified that error appears in the above-identified patent and that said Letters Patent is hereby corrected as shown below:

On the cover page, Item [73] "Kenkyuso" should read -- Kenkyusyo --.

Signed and Sealed this

Sixth Day of April, 1993

*Attest:*

STEPHEN G. KUNIN

*Attesting Officer*  Acting Commissioner of Patents and Trademarks